United States Patent [19]

Papantoniou

[11] 4,048,301

[45] Sept. 13, 1977

[54] SHAMPOO COMPOSITION CONTAINING A DETERGENT AND A GRAFT CATIONIC COPOLYMER

[75] Inventor: Christos Papantoniou, Epinay-sur-Seine, France

[73] Assignee: L'Oreal, Paris, France

[21] Appl. No.: 690,782

[22] Filed: May 27, 1976

[30] Foreign Application Priority Data

May 28, 1975  Luxembourg .......................... 72593

[51] Int. Cl.$^2$ ................................................ A61K 7/06
[52] U.S. Cl. .............................. 424/70; 252/DIG. 2; 252/DIG. 3; 252/DIG. 13; 252/546; 252/547; 424/DIG. 2
[58] Field of Search .................. 252/DIG. 2, DIG. 3, 252/DIG. 13, 546, 547; 424/DIG. 2, 70, 71

[56] References Cited

U.S. PATENT DOCUMENTS

| | | | |
|---|---|---|---|
| 3,769,398 | 10/1973 | Hewitt ................................. | 424/70 |
| 3,849,548 | 11/1974 | Grand ................................. | 424/70 |
| 3,980,769 | 9/1976 | Ghilardi et al. ........................ | 424/70 |

Primary Examiner—Albert T. Meyers
Assistant Examiner—Vera C. Clarke
Attorney, Agent, or Firm—Cushman, Darby & Cushman

[57] ABSTRACT

A cosmetic shampoo composition comprises in a carrier for application to the hair at least one detergent and at least one graft cationic copolymer of N-vinylpyrrolidone, dimethylaminoethyl methacrylate and polyethylene glycol.

8 Claims, No Drawings

SHAMPOO COMPOSITION CONTAINING A DETERGENT AND A GRAFT CATIONIC COPOLYMER

The present invention relates to new shampoo compositions for the treatment of living human hair.

It is known that after a conventional shampoo, the hair very often has a dull look and cannot be easily combed, especially if it is particularly long.

In order to impart luster and softness to the hair an also to facilitate its combing or untangling, certain compositions have been proposed. However, it has been found that these conventional compositions do not provide all the desired results. For instance, it is often very difficult to restore the hair to its original appearance while at the same time rendering the hair easy to comb.

It has now been found that the hair can be restored to its original appearance while facilitating the combing thereof by employing a shampoo composition which includes a particular type graft cationic copolymer.

The present invention thus relates to a shampoo composition for the treatment of hair, comprising in a cosmetic vehicle or carrier applicable to the hair at least one detergent and at least one graft cationic copolymer of:

a. from 3 to 95 weight percent N-vinylpyrrolidone,
b. from 3 to 95 weight percent dimethylaminoethyl methacrylate and
c. from 2 to 50 weight percent polyethylene glycol.

The amount of the polyethylene glycol present in said copolymer is preferably between 5 and 30 weight percent thereof.

It has been observed that the presence of this graft cationic copolymer in the composition of the present invention significantly improves the luster, shine, touch and combing of hair washed with said composition.

In accordance with a particular embodiment of the present invention, the graft cationic copolymer employed is one which is quaternized, completely or partially, with a quaternization agent selected from the group consisting of dimethyl sulfate, diethyl sulfate, benzyl chloride, benzyl iodide and benzyl bromide.

The polyethylene glycol used in producing the graft cationic copolymer of the present invention has, generally, a molecular weight between 200 and several million but, preferably, between 300 and 30,000, while the graft cationic copolymer, as defined above, has a molecular weight ranging between 10,000 and 1,000,000 and preferably between 15,000 and 500,000.

It has also been found that excellent results are obtained when the amount of the graft cationic polymer present in the shampoo composition of this invention ranges between 0.1 and 5 weight percent relative to the total weight of the said shampoo composition.

The detergent employed in the shampoo composition of this invention can be an anionic, nonionic, cationic or amphoteric detergent and is present in the composition in an amount of 0.2 to 25 weight percent relative to the total weight of the composition.

Representative anionic detergents include, for instance, alkyl sulfates, alkyl ether sulfates, alkyl polyether sulfates, alkyl sulfonates, wherein each of the alkyl moieties contains from 8-18 carbon atoms, monoglyceride sulfates, monoglyceride sulfones, alkanolamide sulfates, alkanolamide sulfones, soaps of fatty acids, mono-sulfosuccinates of fatty alcohols, the condensation products of a fatty acid with isethionic acid, the condensation products of a fatty acid with sarcosine and the condensation products of a fatty acid with protein hydrolyzates.

Representative nonionic detergents include, for instance, esters of polyols and sugars, the condensation products of ethylene oxide and a fatty acid, a fatty alcohol, a long chain alkyl phenol, a long chain mercaptan or a long chain amide and polyethers of polyhydroxylated fatty alcohols, i.e. poly glycerols.

Representative cationic detergents include, for instance, long chain quaternary ammoniums, esters of fatty acids and amino alcohol and polyether amines.

Representative amphoteric detergents include, for instance, asparagine derivatives, condensation products of mono-chloroacetic acid and imdiazolines, and alkyl amino-propionates.

The various detergents usefully employed in the shampoo composition of the present invention are described in detail in the article devoted to shampoos by R. G. Harry, "Harry's Cosmeticology", 1973, 6th ed., pages 383 to 390.

In addition to one or more of these detergents, the shampoo composition of the present invention can also contain other conventional adjuvants such as a fatty amide, an amine oxide, a fatty ester, a perfume or a dye. Preferably, these adjuvants are present in an anionic shampoo composition.

The pH of the shampoo composition of the present invention ranges between 4 and 7 and advantageously between 4.5 and 6.5.

The graft cationic copolymer employed in the shampoo composition is obtained in a polymerization reaction carried out in accordance with conventional procedures, i.e. in mass, in suspension, in emulsion or in solution in a solvent. In a preferred manner, the polymerization is carried out in solution.

An initiator for the polymerization reaction can be employed and generally it is a conventional radical polymerization initiator. Representative initiators usefully employed include, for instance, peroxides such as benzoyl peroxide, lauroyl peroxide, acetyl peroxide and benzoyl hydroperoxide.

A polymerization catalyst which on decomposition evolves an inert gas can also be employed. Representative catalysts include azo-bis-isobutyronitrile.

The amount of the initiator employed in the reaction ranges, generally, between 0.2 and 15 and preferably between 0.5 and 12, weight percent relative to the total weight of the initial reactants.

The molecular weight of the graft cationic copolymers can be regulated by introducing during the course of the polymerization a small amount of a chain regulating agent such as an aldehyde, for instance, butyraldehyde or a halogenated compound such as chloroform, bromoform and carbon tetrachloride, or a mercaptan such as lauryl mercaptan, and the like.

The following non-limiting examples are provided to illustrate the present invention.

Examples of Preparing the Graft Cationic Copolymers

EXAMPLE 1

Into a 500 ml round bottomed flask provided with a mechanical stirrer, a condenser, and a thermometer, the following reactants are introduced:

N-vinylpyrrolidone, freshly distilled . . . 50.6 g
Dimethylaminoethyl methacrylate . . . 41.25 g
Polyethylene glycol, MW-20,000 . . . 8.15 g Azo-bis-isobutyronitrile . . . 0.2 g
Ethanol, absolute . . . 20 g The reaction mixture is heated, with agitation, to a temperature of 65° C. When the reaction mixture becomes viscous, an additional 80 g of absolute ethanol previously heated to 65° C are added thereto. The temperature is then raised and maintained at 76° C and the agitation is continued for 24 hours.

After this period of time, 200 g of water are added to the reactor and the water-ethanol azeotrope is distilled until all of the ethanol has been eliminated. There is thus obtained a 98% yield of the desired polymer, having a viscosity of 32 cps, measured in a 2% solution of the polymer in water at a temperature of 34.6° C.

EXAMPLE 2

Into a 500 ml round bottomed flask fitted with a mechanical stirrer, a condenser and a thermometer, the following reactants are introduced:

N-vinylpyrrolidone, freshly distilled . . . 54.62 g
Dimethylaminoethyl methacrylate . . . 9.87 g
Dimethylaminoethyl methacrylate quaternized with dimethyl sulfate . . . 26.70 g
Polyethylene glycol, MW-20,000 . . . 8.81 g
Azo-bis-isobutyronitrile . . . 0.2 g
Ethanol, absolute . . . 20 g By operating as in Example 1, there is thus obtained a 98% yield of the graft cationic copolymer having a viscosity of 11.2 cps, measured in a 2% solution of the polymer in water at a temperature of 34.6° C.

EXAMPLE 3

Into a 3 liter round bottomed flask fitted with a mechanical stirrer and a thermometer, the following reactants are introduced:

N-vinylpyrrolidone . . . 303.6 g
Polyethylene glycol, MW-20,000 . . . 48.9 g
Dimethylaminoethyl methacrylate quaternized with dimethyl sulfate . . . 247.5 g
Azo-bis-isobutyronitrile . . . 12 g
Water, distilled . . . 1400 ml The temperature of this mixture is rapidly elevated to 60° C where the reaction starts and continues. The temperature of the mixture rises to 95°–100° C in about 8 to 12 minutes.

During this phase, a significant thickening of the mass occurs and the temperature of the reaction mass is maintained at 90° C for 1 hour at the termination of the exothermicity. At this time, analysis indicates a reaction rate for each of the monomers greater than 99%

The product obtained which is colorless and perfectly water-soluble has a viscosity measured in a 2% aqueous solution of the polymer at 34.6° C, between 22 and 28 cps.

EXAMPLE 4

Into a 500 ml round bottomed flask, fitted with a mechanical stirrer, a condenser and a thermometer, the following reactants are introduced:

N-vinylpyrrolidone, freshly distilled . . . 50.6 g
Dimethylaminoethyl methacrylate quaternized with dimethyl sulfate . . . 41.25 g
Polyethylene glycol, MW-20,000 . . . 8.15 g
Azo-bis-isobutyronitrile . . . 0.2 g
Ethanol, absolute . . . 100 g The reaction mixture is initially heated to 65° C for 4 hours, then at 80° C for 20 hours. After this time, 200 g of water are introduced into the reactor and the water-ethanol azeotrope is distilled until all the ethanol has been eliminated.

There is thus obtained a 97% yield of the desired polymer, having a viscosity of 12.45 cps, measured in a 2% solution of the polymer in water at a temperature of 34.6° C.

EXAMPLE 5

Into a 500 ml round bottomed flask, provided with a mechanical stirrer, a condenser, a thermometer and a nitrogen lead-in tube, the following reactants are introduced:

N-vinylpyrrolidone, freshly distilled . . . 50.6 g
Dimethylaminoethyl methacrylate quaternized with dimethyl sulfate . . . 41.25 g
Polyethylene glycol, MW-20,000 . . . 8.15 g
Water . . . 100 g The mixture is heated with agitation to 40° C until the polyethylene glycol is completely dissolved, at which time sufficient borax ($Na_2B_4O_7.10H_2O$) is introduced to adjust the pH to 9. Thereafter 1 ml $H_2O_2$ (30%) is added to the reaction medium and the heating thereof is continued at 40° C for 12 hours.

The solution at the end of the polymerization reaction is viscous but stirrable, and the resulting polymer is obtained in a 98% yield, having a viscosity of 8.46 cps, measured in a 2% solution of the polymer in water at 34.6° C. Examples of Compositions

EXAMPLE A

An anionic shampoo composition is prepared in accordance with the present invention by admixing the following components:

Triethanolamine lauryl myristyl sulfate . . . 12 g
Diethanolamide of copra . . . 2 g
Myristyl dimethyl amine oxide . . . 1.5 g
Graft cationic copolymer of Example 2 . . . 1.5 g
Lactic acid, q.s.p. pH = 6.5
Water, q.s.p. . . . 100 g This shampoo composition which is present in a clear form exhibits excellent cosmetic properties. After its application to the hair, the combing of the wet hair is quite easy and the hair drying is shiny, soft and flexible.

EXAMPLE B

An anionic shampoo composition is prepared in accordance with the present invention by admixing the following components:

Sodium lauryl ether sulfate oxyethylenated with 2.2 moles of ethylene oxide . . . 10 g
Diethanolamide of copra . . . 3 g
Sodium N-lauryl sarcosinate . . . 4 g
Glycol distearate . . . 2 g
Graft cationic copolymer of Example 1 . . . 1 g
Water, q.s.p. . . . 100 g This shampoo composition when applied to the hair exhibits good foaming and detergent power and imparts to the hair a very good luster, the hair being easy to comb.

EXAMPLE C

A nonionic shampoo composition is prepared in accordance with the invention by admixing the following components:

$C_{11}$-$C_{14}$ diol polyglycerolated with 3-4 moles of glycerol . . . 17 g
Graft cationic copolymer of Example 3 . . . 2 g
Cetyl pyridinium chloride . . . 0.8 g Lauryl diethanolamine . . . 2.5 g
Perfume . . . 0.2 g
Lactic acid, q.s.p. pH = 5.5
Water, q.s.p. . . . 100 ml This shampoo composition is a soft and clear cream and provides abundant foam when applied to the hair. After shampooing with the above composition, the wet hair, be it natural, dyed or bleached, is easily combed. After drying, the hair is soft, light and shiny.

EXAMPLE D

A cationic shampoo composition is prepared in accordance with the invention by admixing the following components:

Cetyl trimethyl ammonium bromide . . . 2 g
Lauryl alcohol polyglycerolated with 4 moles of glycerol . . . 12 g
Graft cationic copolymer of Example 2 . . . 1 g
Perfume . . . 0.2 g
Lactic acid, q.s.p. pH = 4.5
Water, q.s.p. . . . 100 ml This shampoo composition is present in a clear form and when applied to the hair, it produces a light and airy foam. After shampooing with this composition, the wet hair is easily combed. After drying, the hair is soft, very shiny and exhibits a light appearance.

This Example is repeated except that the copolymer prepared in accordance with Example 2 is advantageously replaced by the same amount of the polymer prepared in one instance according to Example 4 and in another instance according to Example 5.

What is claimed is:

1. A cosmetic shampoo composition for treating the hair comprising a cosmetic carrier for application to the hair, at least one detergent in an amount between 0.2 and 25 weight percent based on the total weight of said composition and at least one graft cationic polymer of
   a. 3 to 95 weight percent N-vinylpyrrolidone,
   b. 3 to 95 weight percent dimethylaminoethyl methacrylate, and
   c. 2 to 50 weight percent polyethylene glycol,
said graft cationic copolymer being present in an amount between 0.1 and 5 weight percent based on the total weight of said composition and having a molecular weight ranging between 10,000 and 1,000,000.

2. The composition of claim 1 which also includes an adjuvant selected from the group consisting of a fatty amide, an amine oxide, a fatty ester and a perfume.

3. The composition of claim 1 wherein the said graft cationic copolymer is quaternized with a quaternization agent.

4. The composition of claim 3 wherein said quaternization agent is selected from the group consisting of dimethyl sulfate, diethyl sulfate, benzyl chloride, benzyl iodide and benzyl bromide.

5. The composition of claim 1 wherein said graft cationic copolymer has a molecular weight between 15,000 and 500,000.

6. The composition of claim 1 wherein said detergent is selected from the group consisting of an anionic, a nonionic, a cationic and an amphoteric detergent.

7. The composition of claim 1 wherein the carrier is an aqueous carrier and having a pH between 4 and 7.

8. The composition of claim 1 wherein the carrier is an aqueous carrier and having a pH between 4.5 and 6.5.

* * * * *